(12) United States Patent
Kim et al.

(10) Patent No.: US 11,452,679 B2
(45) Date of Patent: Sep. 27, 2022

(54) METHOD OF PREPARING BIOACTIVE SUBSTANCE-ENCAPSULATED ETHOSOME, ETHOSOME COMPOSITION, AND COSMETIC COMPOSITION INCLUDING ETHOSOME COMPOSITION

(71) Applicant: BINOTEC CO., LTD., Daegu (KR)

(72) Inventors: Yu Mi Kim, Daegu (KR); Gi Hyun Jang, Daegu (KR)

(73) Assignee: BINOTEC CO., LTD., Daegu (KR)

( * ) Notice: Subject to any disclaimer, the term of this patent is extended or adjusted under 35 U.S.C. 154(b) by 0 days.

(21) Appl. No.: 16/498,295

(22) PCT Filed: Mar. 9, 2018

(86) PCT No.: PCT/KR2018/002808
§ 371 (c)(1),
(2) Date: Sep. 26, 2019

(87) PCT Pub. No.: WO2019/004563
PCT Pub. Date: Jan. 3, 2019

(65) Prior Publication Data
US 2021/0030640 A1 Feb. 4, 2021

(30) Foreign Application Priority Data
Jun. 30, 2017 (KR) .................. 10-2017-0083071

(51) Int. Cl.
*A61K 8/14* (2006.01)
*A61K 8/55* (2006.01)
*A61K 8/63* (2006.01)
*A61K 8/64* (2006.01)
*A61Q 19/00* (2006.01)

(52) U.S. Cl.
CPC ............... *A61K 8/14* (2013.01); *A61K 8/553* (2013.01); *A61K 8/63* (2013.01); *A61K 8/64* (2013.01); *A61Q 19/00* (2013.01)

(58) Field of Classification Search
None
See application file for complete search history.

(56) References Cited

U.S. PATENT DOCUMENTS 5,540,934 A 7/1996 Touitou
2009/0047234 A1 2/2009 Touitou et al.

FOREIGN PATENT DOCUMENTS

| DE | 695 12 685 T2 | 5/2000 |
| KR | 10-2014-0054698 A | 5/2014 |
| KR | 10-2014-0101570 A | 8/2014 |
| KR | 10-2016-0073192 A | 6/2016 |
| KR | 10-2017-0043132 A | 4/2017 |
| KR | 10-1810160 B1 | 1/2018 |
| WO | WO 2013/012101 A1 | 1/2013 |

OTHER PUBLICATIONS

Shahi et al., "Development and evaluation of Cosmeceutical Nanolipogel", Research Journal of Topical and Cosmetic Sciences, 1(1), 2010, pp. 18-24. (Year: 2010).*
Touitou et al, "Enhanced Delivery of Drugs Into and Across the Skin by Ethosomal Carriers", Drug Development Research, 50, 2000, pp. 406-415. (Year: 2000).*
Jain et al., "Formulation and rheological evaluation of ethosome-loaded carbopol hydrogel for transdermal application", Drug Development and Industrial Pharmacy, 42(8), 2016, pp. 1315-1324. (Year: 2016).*
Shahi et al. "Development and evaluation of Cosmeceutical Nanolipogel", Research J. Topical and Cosmetic Sci, 1(1), 2010, pp. 18-24. (Year: 2010).*
Jain et al., "Quality by design approach for formulation, evaluation and statistical optimization of diclofenacloaded ethosomes via transdermal route", Pharmaceutical Development and Technology, 20(4), 2015, pp. 473-489. (Year: 2015).*
Pai et al., "Topical peptides as cosmeceuticals", . Indian J Dermatol Venereol Leprol, 83(9), 2017, pp. 9-18. (Year: 2017).*
Verma et al., "Therapeutic and cosmeceutical potential of ethosomes: An overview", J Adv Pharm Technol Res., 1(3), 2010, pp. 274-282. (Year: 2010).*
International Search Report and Written Opinion dated Jun. 8, 2018 in PCT/KR2018/002808 filed on Mar. 9, 2018.
Adachi, T. et al., "Interdigitated Structure of Phospholipid-Alcohol Systems Studied by X-Ray Diffraction," Biophysical Journal, vol. 68, May 1995, pp. 1850-1855.
Dubey, V. et al., "Dermal and transdermal delivery of an antipsoriatic agent via ethanolic liposomes," Elsevier, ScienceDirect, Journal of Controlled Release, vol. 123, 2007, pp. 148-154.
Dubey, V. et al., "Melatonin loaded ethanolic liposomes: Physicochemical characterization and enhanced transdermal delivery," Elsevier, ScienceDirect, European Journal of Pharmaceutics and Biopharmaceutics, vol. 67, 2007, pp. 398-405.
German Office Action dated Nov. 4, 2021 in German Patent Application No. 10 2018 003 377.5 (with English translation), 12 pages.

* cited by examiner

*Primary Examiner* — Melissa L Fisher
(74) *Attorney, Agent, or Firm* — Oblon, McClelland, Maier & Neustadt, L.L.P.

(57) ABSTRACT

Provided is a method of preparing a bioactive substance-encapsulated ethosome, the method including: preparing an aqueous solution of a bioactive substance, preparing a lipid-dissolved solution by dissolving lipids in ethanol, preparing a hydrated liquid crystalline phase by hydrating the lipid-dissolved solution by mixing and agitating the bioactive substance aqueous solution together with the lipid-dissolved solution, and preparing an ethosome solution by adding purified water to the hydrated liquid crystalline phase to produce a mixture and agitating the mixture.

10 Claims, 5 Drawing Sheets

[Fig. 1]
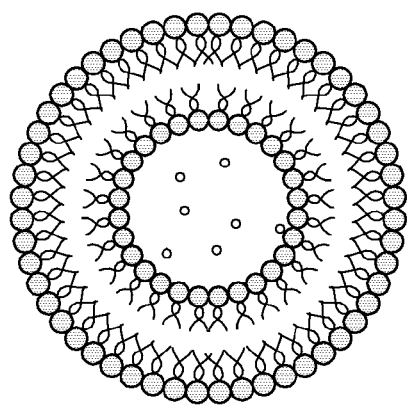
(a)
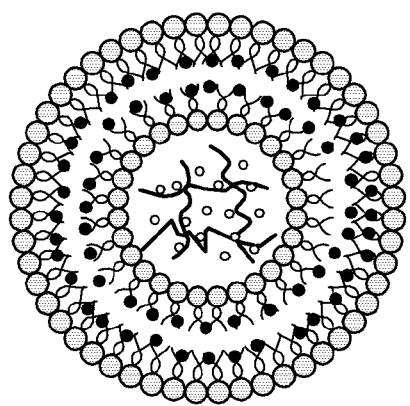
(b)
⌇⌇ : HYDROGEL
○ : PEPTIDE
● : ETHANOL

[Fig. 2]
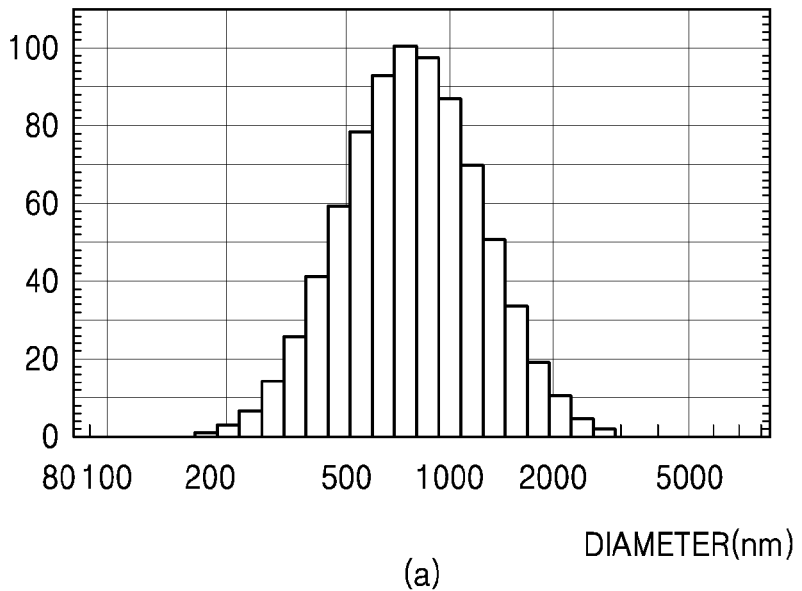
(a)
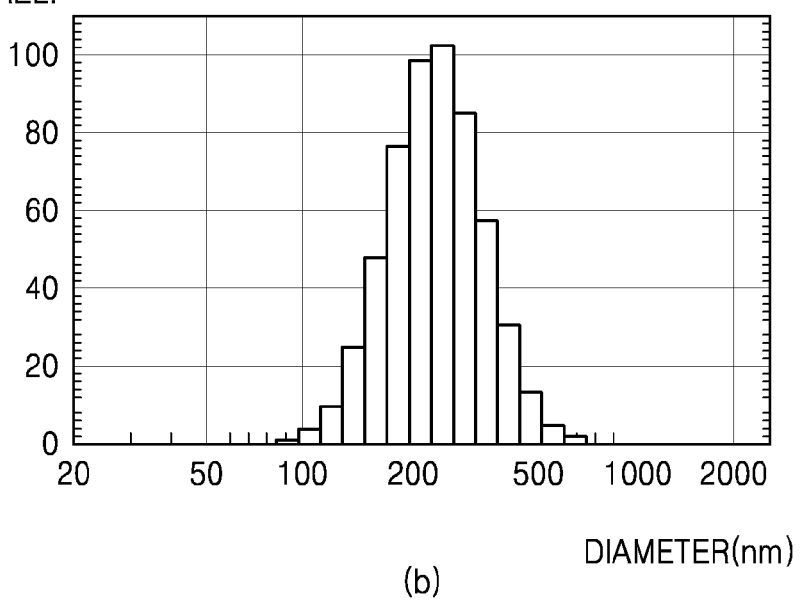
(b)

[Fig. 3]
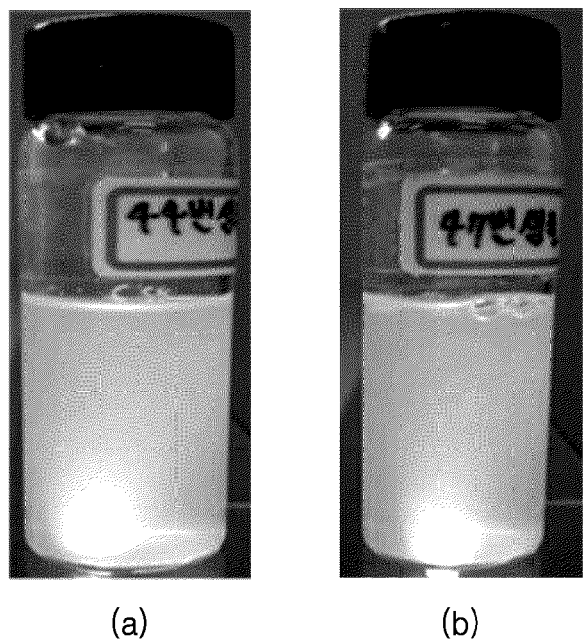
(a)         (b)
[Fig. 4]
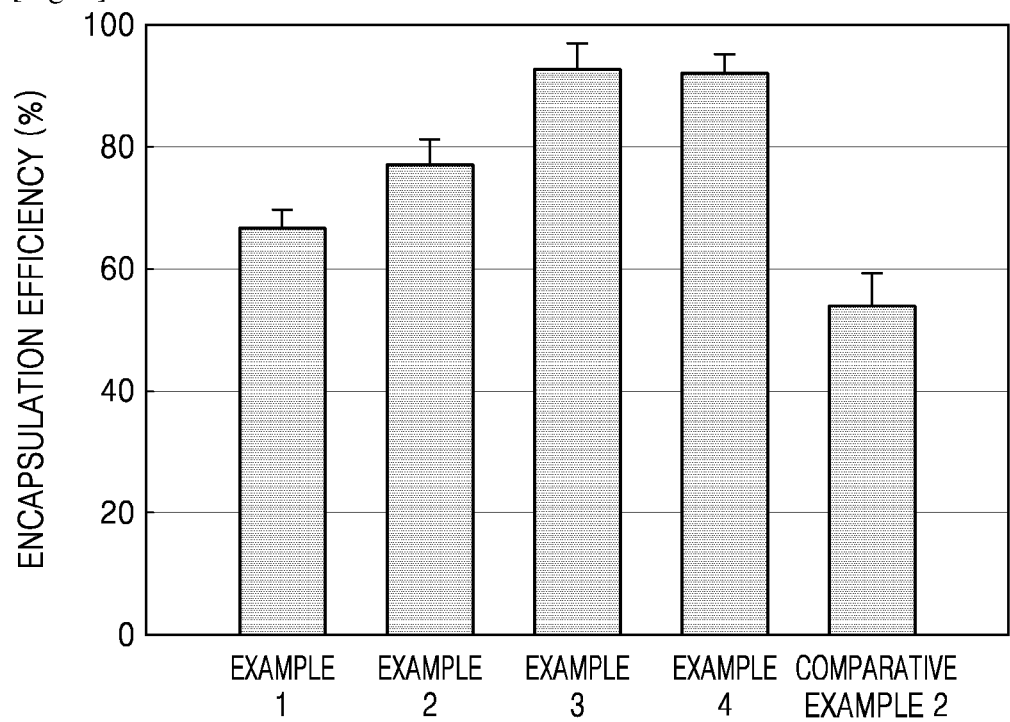

[Fig. 5]
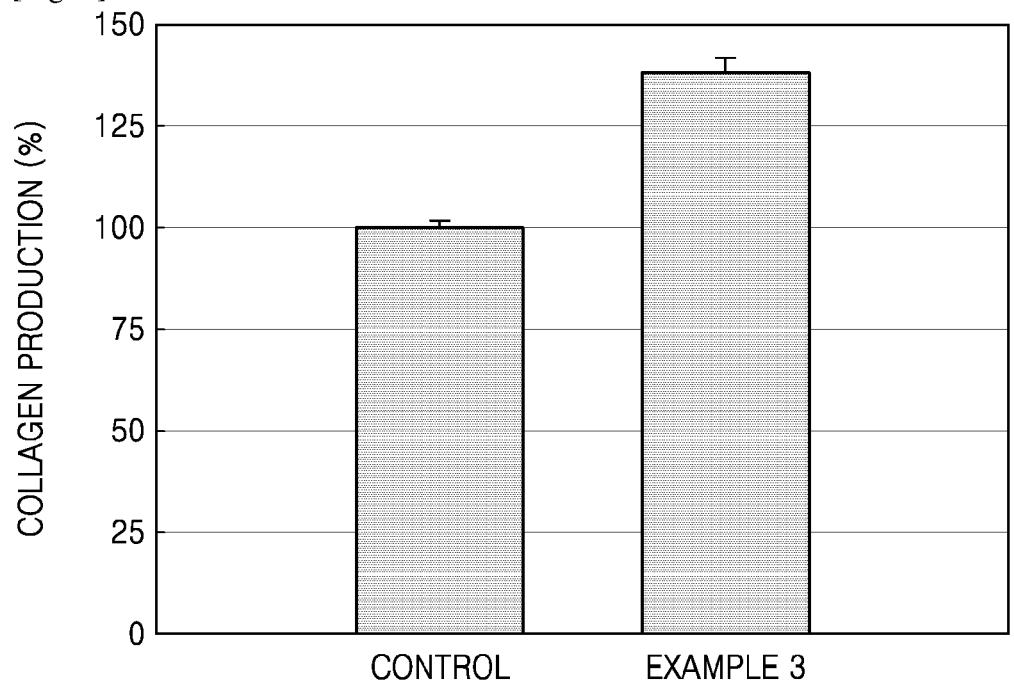
[Fig. 6]
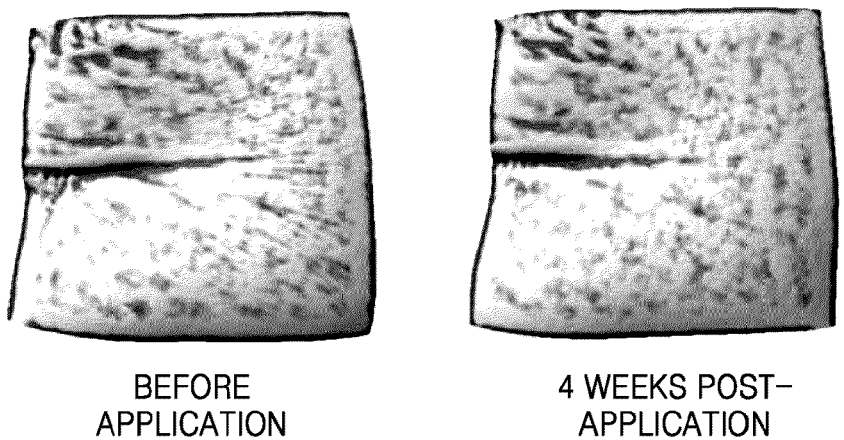
BEFORE APPLICATION　　　4 WEEKS POST-APPLICATION

[Fig. 7]
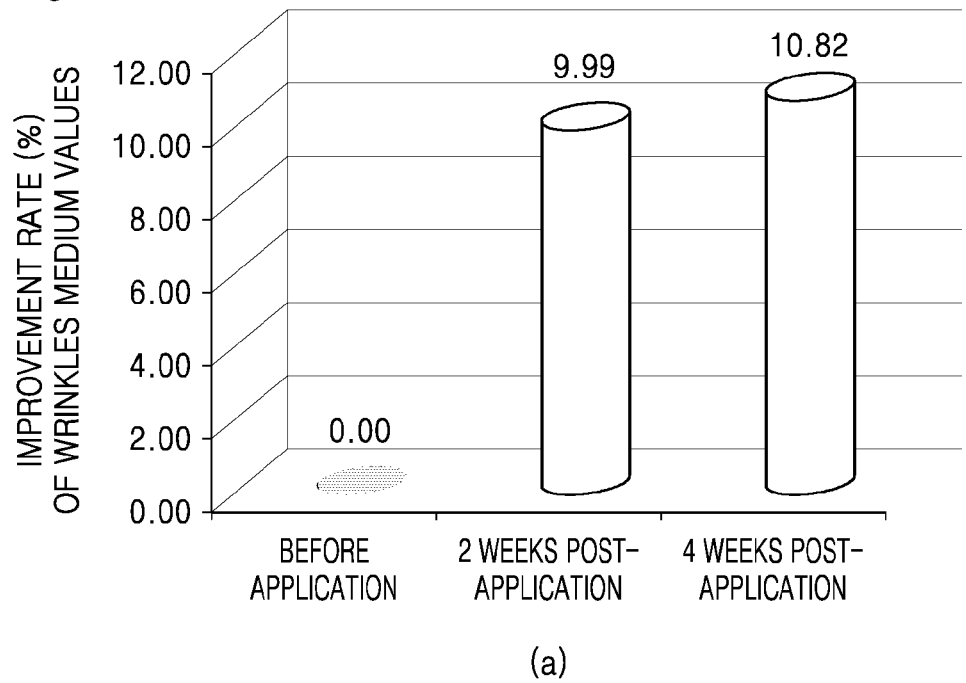
(a)
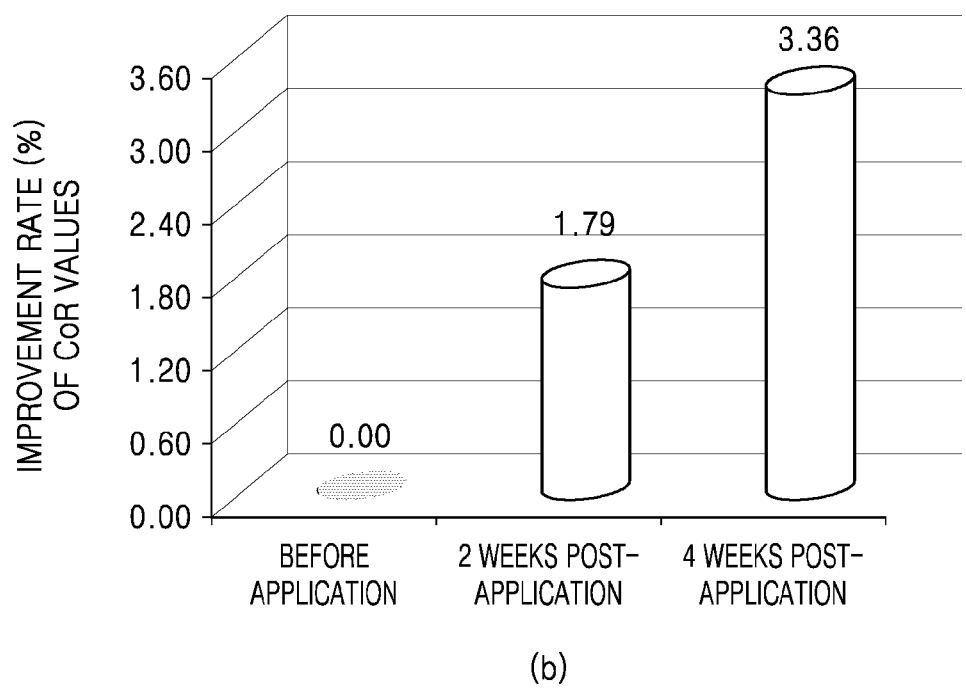
(b)

METHOD OF PREPARING BIOACTIVE SUBSTANCE-ENCAPSULATED ETHOSOME, ETHOSOME COMPOSITION, AND COSMETIC COMPOSITION INCLUDING ETHOSOME COMPOSITION

CROSS-REFERENCE TO RELATED APPLICATION

Background Art

The present disclosure relates to a method of preparing a bioactive substance-encapsulated ethosome, and a composition including the same.

Technical Field

This application claims the benefit of Korean Patent Application No. 10-2017-0083071, filed on Jun. 30, 2017, in the Korean Intellectual Property Office, the disclosure of which is incorporated herein in its entirety by reference.

Description of the Related Art

Skin surrounds the whole body and is largely composed of three layers: the epidermis, dermis, and hypodermis. Among these, the epidermis is the outermost layer and includes the stratum corneum, which functions as a skin barrier protecting the human body from various external stimuli. The stratum corneum is made up of multiple layers of flattened keratinocytes, and the keratinocytes are filled with a hydrophobic insoluble fibrous protein called keratin. Keratinocytes are embedded in a lamellar structure filled with intercellular lipids consisting of ceramides, free fatty acids, cholesterol, etc. Due to these structural features, the stratum corneum inhibits evaporation of water from the skin surface and effectively protects the body against external stress or harmful stimuli. However, this skin protection mechanism of the stratum corneum makes it very difficult for cosmetics containing highly functional ingredients to penetrate the stratum corneum and to be absorbed into the dermis to substantially influence cellular mechanisms.

The cosmetics industry has continued to study methods of absorption of cosmetics components into cell membranes as much as possible to cause the components to penetrate cell membranes and to influence cellular mechanisms. The drug delivery formulations most commonly used to increase transdermal absorption rates are liposomes. Liposomes are drug delivery carriers composed of a lipid bilayer similar to a cell membrane and capable of enclosing a water-soluble bioactive substance. Liposomes have been widely used in medicines and cosmetics, because they are able to deliver various active materials in vivo and have high biocompatibility.

However, various modified liposomes have been actively studied because of problems of physical instability of the lipid bilayer membrane constituting the liposomes, low emulsion stability, and low encapsulation efficiency of active ingredients. Representative examples of such modified liposomes are ethosomes and elastic liposomes. An ethosome is the carrier with the highest transdermal absorption rate investigated so far, since it includes ethanol in order to have a higher transdermal absorption rate than a liposome, which provides reduced surface tension of phospholipids, and also imparts flexibility to the membrane of the vesicle itself.

Ethosomes which are directly applied to the skin as a cosmetic material have problems due to their low encapsulation efficiency and high ethanol content. The ethanol content in the ethosomes which have been developed until now is very high, at up to 20% to 40%. For example, Korean Patent Publication No. 10-2014-0101570 discloses ethosomes containing an extract of *Persicaria hydropiper* L., of which ethanol content is 20% or more. Further, U.S. Pat. No. 5,540,934 also discloses a composition having an ethanol content of 20% to 46%. However, application of ethosomes of high ethanol content to cosmetic materials is disadvantageous in that it is difficult to apply ingredients of a high content and the ethosomes may cause skin irritation. In addition, ethanol promotes moisture evaporation from the skin, which dries the skin, and therefore, the ethosomes are not suitable as a cosmetic ingredient. Further, ethosomes have a disadvantage in terms of low encapsulation efficiency due to high flexibility of vesicular membranes. For example, as disclosed in the above-described Korean Patent Publication No. 10-2014-0101570, when 0.1% isoquercitrin is encapsulated in ethosomes, the encapsulation efficiency is 54%, indicating that about half of the material to be encapsulated in the ethosomes is not captured in the carrier but dissolved in the solution. In other words, it means that although the transdermal absorption rate of ethosome is very high, the drug delivery efficiency is not high.

Accordingly, ethosomes that have the highest transdermal absorption rate as compared to conventional carriers need to be developed as carriers having high encapsulation efficiency and a suitable ethanol content for a cosmetic ingredient.

PRIOR ART DOCUMENTS

Patent Documents (Patent Document 0001) U.S. Pat. No. 5,540,934
(Patent Document 0002) Korean Patent Publication No. 10-2014-0101570

DISCLOSURE OF INVENTION

Technical Problem

SUMMARY

In the prior art, ethosomes containing 20% or more of ethanol have a very high transdermal absorption rate but have a disadvantage in that they cause high skin irritation when used as a cosmetic ingredient. Further, such ethosomes have very low drug encapsulation efficiency, as compared with known liposomes, and thus it is difficult to enhance their drug delivery efficiency. The known ethosomes could be prepared in a nanoparticle size of 150 nm to 250 nm on average by using a relatively high content of ethanol. However, when the ethanol content is decreased in the known ethosomes, the nanoparticle size is increased, and therefore, transdermal absorption rates of the ethosomes cannot be increased. Further, the known ethosomes have been prepared by a film hydration method which is not suitable for mass-production.

A technology described below is intended to provide a nanoethosomal delivery composition having ethanol content suitable for cosmetic ingredients, and a preparation method thereof.

The technology described below is intended to provide an ethosomal delivery composition with remarkably improved encapsulation efficiency and stability, as compared with the known ethosomes, and a preparation method thereof.

The technology described below is intended to provide a method of preventing an increase in nanoparticle size which occurs when the ethanol content in the known ethosomes is decreased, by using a high-pressure homogenizer.

The technology described below is intended to provide a method of preparing an ethosome suitable for mass-production.

The technology described below is intended to provide an ethosome composition, in which a peptide which is a bioactive material having a remarkable wrinkle-improving effect is encapsulated, and a preparation method thereof.

The technology described below is intended to provide a novel ethosome structure, in which a hydrogel is encapsulated together with a drug by physical or chemical binding in order to further improve encapsulation efficiency and stability, a composition including the structure, and a preparation method thereof.

Furthermore, the technology described below is intended to provide a cosmetic composition including a peptide- or a peptide-hydrogel complex-encapsulated ethosome.

Solution to Problem

DETAILED DESCRIPTION

Ethosome is a drug delivery system for enhancing skin absorption effect of liposome, and is a deformable formulation with more flexible membrane than liposome, which is able to easily pass through the narrow space between corneocytes (Dubey et al., 2007). Ethosome is prepared by dissolving phospholipids in ethanol which is known as a skin permeation enhancer. Ethanol acts on polar heads of lipids to reduce surface tension, thereby reducing surface tension of lipid membranes in the stratum corneum and making the membrane of the vesicle itself flexible (Dubey et al., 2007). Due to these features, ethosomes are effective for delivery of active ingredients into the skin, and are able to deliver active ingredients to the deeper layers of the skin (Adachi et al., 1995).

Such characteristics of ethosomes are attributed to nanoliposomes containing ethanol. The content of ethanol in ethosome is 20% or more, and ethanol is a substance that dehydrates and irritates the skin because ethanol evaporates along with the moisture of the skin when it is in contact with the skin. For this reason, as the ethanol content is higher, the skin irritation becomes more severe. In addition, since ethanol makes the lipid membrane flexible, there is a disadvantage that ethanol reduces drug encapsulation.

Characteristics of ethosome suggested below are developed to increase encapsulation efficiency and to decrease the skin irritation as suitable for cosmetic ingredients by optimizing the content of ethanol. Hereinafter, a novel ethosome will be described in detail. FIG. 1 illustrates example structures of a known liposome and a novel nanoethosome. FIG. 1(a) illustrates the structure of the known liposome, and FIG. 1(b) illustrates the structure of the nanoethosome. Referring to FIG. 1(b), a support may be a liposome including ethanol. The ethosome includes ethanol in the phospholipid layer, for example, in a hydrophobic region of the phospholipid bilayer. In FIG. 1(b), a subject to be support is a complex of a peptide and a hydrogel. For example, the complex of a peptide and a hydrogel may be included in a aqueous solution core surrounded by the phospholipid layer.

Phospholipids constituting the ethosome may be a natural phospholipid and/or a synthetic lipid. The natural phospholipid may be at least one selected from the group consisting of cholesterol, egg yolk lecithin (phosphatidylcholine), soybean lecithin, lysolecithin, sphingomyelin, phosphatidic acid, phosphatidylserine, phosphatidyl-glycerol, phosphatidylinositol, phosphatidylethanolamine, diphosphatidylglycerol, cardiolipin, and plasmalogen. A proportion of the phospholipids in all components of the ethosome is preferably less than 0.1 wt % to 10 wt %. More preferably, the proportion of the phospholipids in all components of the ethosome is 1 wt % to 4 wt %. When the proportion of the phospholipids in all components of the ethosome is less than 0.1 wt %, it is difficult to encapsulate a drug inside the ethosome. When the proportion of the phospholipids in all components of the ethosome is 10 wt % or more, it is difficult to dissolve the phospholipids in an aqueous solution, and dispersion is decreased, and therefore, nanoparticles may not be obtained.

The synthetic lipid may be at least one selected from the group consisting of dicetyl phosphate, distearoylphosphatidylcholine, dioleoylphosphatidylethanolamine, dipalmitoylphosphatidylcholine, dipalmitoylphosphatidylethanolamine, dipalmitoylphos-phatidylserine, eleostearoylphosphatidylcholine, eleostearoylphos-phatidylethanolamine, and eleostearoylphosphatidylserine. A proportion of the synthetic lipid is preferably 0 wt % to 0.1 wt %. Although the synthetic lipid is not necessarily included in the components of ethosome, it is preferably included in an amount of less than 0.1 wt % to improve encapsulation efficiency. When the synthetic lipid is included in an amount of 0.1 wt % or more in the ethosome, nanoparticles are not stabilized and tend to rapidly release the internal drug.

When cholesterol is added as a lipid component, it contributes to more stable formation of liposome. Cholesterol is wedged between phospholipids to make the membrane structure more rigid, and therefore, contributing to formation of a stable phospholipid membrane. Therefore, a proportion of cholesterol in all components of the ethosome is preferably 0.01 wt % to 0.5 wt %. The proportion of cholesterol in all components of the ethosome is more preferably 0.1 wt % to 0.2 wt %. A proper amount of cholesterol stabilizes the phospholipid membrane to contribute to particle stability.

Ethanol which is the most important component of the ethosome plays a role in making the lipid membrane flexible to increase a transdermal absorption rate. A size of nanoparticles, encapsulation efficiency, lipid flexibility, etc. may be greatly changed according to the content of ethanol, and therefore, the proportion of ethanol is very important. A proportion of ethanol in all components of the ethosome is preferably 0.1 wt % to 20 wt %. The proportion of ethanol in all components of the ethosome is more preferably 2 wt % to 8 wt %.

When the content of ethanol is too low, the transdermal absorption rate may not be increased. When the content of ethanol is too high, skin irritation is increased and a drug is released therefrom. Thus, the ethosome becomes useless.

A kind of the drug to be encapsulated is not limited to cosmetic ingredients or medical ingredients. The drug may be any of water-soluble and water-insoluble drugs. All substances having bioactive effects are possible. Hereinbelow, a specific peptide will be described as a bioactive substance, but is not limited thereto.

The peptide is a unit of a particular arrangement of amino acids, and penetrates the cell membrane and influences cellular mechanisms. The peptide as a cosmetic ingredient influences cellular mechanisms involved in wrinkle improvement, skin whitening, etc. to impart high functionality to cosmetics. For example, the peptide is at least one selected from the group consisting of acetyl decapeptide-3, acetyl oligopeptide-2 amide, acetyl tetrapeptide-2, acetyl tetrapeptide-3, acetyl tetrapeptide-5, acetyl tetrapeptide-9, acetyl tetrapeptide-11, acetyl tetrapeptide-15, acetyl tetrapeptide-17, acetyl tetrapeptide-22, acetyl tetrapeptide-40, acetyl tripeptide-1, acetyl pentapeptide-1, acetyl pentapeptide-55 amide, acetyl hexapeptide-1, acetyl hexapeptide-8, acetyl hexapeptide-22, acetyl hexapeptide-30, acetyl hexapeptide-37, acetyl hexapeptide-38, acetyl hexapeptide-39, acetyl hexapeptide-49, acetyl hexapeptide-51 amide, acetyl heptapeptide-4, acetyl heptapeptide-9, palmitoyl tetrapeptide-3, palmitoyl tetrapeptide-7, palmitoyl pentapeptide-3, palmitoyl pentapeptide-4, palmitoyl pentapeptide-5, palmitoyl tripeptide-1, palmitoyl tripeptide-5, palmitoyl tripeptide-8, palmitoyl tripeptide-29, palmitoyl tripeptide-36, palmitoyl tripeptide-38, palmitoyl tripeptide-40, palmitoyl hexapeptide-12, palmitoyl hexapeptide-14, palmitoyl hexapeptide-15, palmitoyl hexapeptide-56, palmitoyl heptapeptide-5, coppertripeptide-1, oligopeptide-1, oligopeptide-2, oligopeptide-3, oligopeptide-4, oligopeptide-5, oligopeptide-6, oligopeptide-7, oligopeptide-11, oligopeptide-14, oligopeptide-18, oligopeptide-20, oligopeptide-24, oligopeptide-27, oligopeptide-28, oligopeptide-29, oligopeptide-30, oligopeptide-31, oligopeptide-32, oligopeptide-34, oligopeptide-41, oligopeptide-42, oligopeptide-50, oligopeptide-51, oligopeptide-52, oligopeptide-54, oligopeptide-55, oligopeptide-57, oligopeptide-58, oligopeptide-59, oligopeptide-61, oligopeptide-62, oligopeptide-66, oligopeptide-68, oligopeptide-70, oligopeptide-71, oligopeptide-72, oligopeptide-73, oligopeptide-74, oligopeptide-75, oligopeptide-76, oligopeptide-79, oligopeptide-86, oligopeptide-88, oligopeptide-92, rh-oligopeptide-1, rh-oligopeptide-2, rh-oligopeptide-4, rh-oligopeptide-33, tripeptide-1, tripeptide-2, tripeptide-3, tripeptide-29, tripeptide-31, tripeptide-32, tripeptide-47, tripeptide-48, tripeptide-56, tetrapeptide-3, tetrapeptide-4, tetrapeptide-7, tetrapeptide-14, tetrapeptide-21, tetrapeptide-26, tetrapeptide-30, tetrapeptide-32, tetrapeptide-42, tetrapeptide-44, tetrapeptide-51, tetrapeptide-56, tetrapeptide-57, tetrapeptide-58, tetrapeptide-59, nicotinoyl hexapeptide-44, nicotinoyl hexapeptide-45, nicotinoyl hexapeptide-56, nicotinoyl dipeptide-22, nicotinoyl dipeptide-23, nicotinoyl dipeptide-24, nicotinoyl dipeptide-26, nicotinoyl tripeptide-1, nicotinoyl tripeptide-35, nicotinoyl tripeptide-47, nicotinoyl tripeptide-48, nicotinoyl octapeptide-9, nicotinoyl pentapeptide-20, nicotinoyl pentapeptide-33, galloyl nonapeptide-11, galloyl tetrapeptide-19, galloyl tripeptide-47, galloyl tripeptide-48, galloyl tripeptide-35, galloyl tripeptide-7, galloyl pentapeptide-33, galloyl hexapeptide-44, digalloyl tetrapeptide-19, de-capeptide-2, decapeptide-4, decapeptide-6, decapeptide-10, decapeptide-11, de-capeptide-12, decapeptide-15, decapeptide-16, decapeptide-18, decapeptide-19, de-capeptide-20, decapeptide-23, decapeptide-25, decapeptide-28, decapeptide-31, retinoyl tripeptide-1, retinoyl tripeptide-35, retinoyl pentapeptide-4, manganese tripeptide-1, mevalonoyl pentapeptide-37, mevalonoyl pentapeptide-39, mevalonoyl tripeptide-1, mevalonoyl tripeptide-35, mevalonoyl tetrapeptide-36, myristoyl tetrapeptide-6, myristoyl tetrapeptide-8, myristoyl tetrapeptide-34, myristoyl tripeptide-31, myristoyl pentapeptide-8, myristoyl pentapeptide-9, myristoyl pentapeptide-17, biotinoyl tetrapeptide-51, biotinoyl tripeptide-1, biotinoyl tripeptide-35, biotinoyl pentapeptide-4, valprooyl oligopeptide-33, caffeoyl decapeptide-17, caffeoyl oligopeptide-77, caffeoyl tripeptide-1, caffeoyl tripeptide-7, caffeoyl tripeptide-35, caffeoyl pentapeptide-20, caffeoyl pentapeptide-27, caffeoyl hexapeptide-48, caffeoyl hexapeptide-50, caffeoyl hexapeptide-56, caffeoyl hexapeptide-65, caffeoyl hep-tapeptide-11, sh-polypeptide-1, sh-polypeptide-2, sh-polypeptide-3, sh-polypeptide-4, sh-polypeptide-5, sh-polypeptide-6, sh-polypeptide-7, sh-polypeptide-8, sh-polypeptide-9, sh-polypeptide-10, sh-polypeptide-11, sh-polypeptide-13, sh-polypeptide-15, sh-polypeptide-16, sh-polypeptide-17, sh-polypeptide-18, sh-polypeptide-19, sh-polypeptide-22, sh-polypeptide-25, sh-polypeptide-26, sh-polypeptide-28, sh-polypeptide-29, sh-polypeptide-31, sh-polypeptide-33, sh-polypeptide-34, sh-polypeptide-35, sh-polypeptide-36, sh-polypeptide-37, sh-polypeptide-38, sh-polypeptide-39, sh-polypeptide-40, sh-polypeptide-41, sh-polypeptide-42, sh-polypeptide-43, sh-polypeptide-44, sh-polypeptide-45, sh-polypeptide-46, sh-polypeptide-50, sh-polypeptide-53, sh-polypeptide-54, sh-polypeptide-55, sh-polypeptide-56, sh-polypeptide-58, sh-polypeptide-59, sh-polypeptide-60, sh-polypeptide-62, sh-polypeptide-64, sh-polypeptide-66, sh-polypeptide-70, sh-polypeptide-71, sh-polypeptide-74, sh-polypeptide-78, sh-polypeptide-81, sh-polypeptide-85, rh-polypeptide-1, rh-polypeptide-2, rh-polypeptide-3, rh-polypeptide-4, rh-polypeptide-5, rh-polypeptide-6, rh-polypeptide-7, rh-polypeptide-8, rh-polypeptide-9, rh-polypeptide-10, rh-polypeptide-11, rh-polypeptide-13, rh-polypeptide-14, rh-polypeptide-15, rh-polypeptide-22, rh-polypeptide-26, rh-polypeptide-28, rh-polypeptide-33, rh-polypeptide-51, rh-polypeptide-53, rh-polypeptide-58, rh-polypeptide-59, rh-polypeptide-60, rh-polypeptide-62, rh-polypeptide-64, rh-polypeptide-66, rh-polypeptide-67, nonapeptide-1, nonapeptide-10, nonapeptide-11, nonapeptide-16, nonapeptide-18, nonapeptide-19, oat peptide, soybean polypeptide, dipeptide-1, dipeptide-15, wheat peptide, salicyloyl octapeptide-9, salicyloyl pentapeptide-33, shikimoyl nonapeptide-11, shikimoyl pen-tapeptide-33, shikimoyl hexapeptide-48, azelaoyl octapeptide-9, azelaoyl tripeptide-1, azelaoyl pentapeptide-37, pea peptide, ursoloyl tetrapeptide-37, ursoloyl tripeptide-1, ursoloyl tripeptide-35, ursoloyl pentapeptide-4, thioctoyl tripeptide-1, thioctoyl tripeptide-35, thioctoyl pentapeptide-4, copper palmitoyl heptapeptide-14, caprooyl tetrapeptide-3, capryloyl dipeptide-17, capryloyl heptapeptide-33, quinoyltripeptide-1, quinoyl tripeptide-7, quinoyltripeptide-35, cocoyl pentapeptide-9, coumaroyl non-apeptide-29, coumaroyl dipeptide-3, pentapeptide-3, pentapeptide-13, pentapeptide-18, pentapeptide-20, pentapeptide-27, pentapeptide-28, pentapeptide-31, pentapeptide-36, pentapeptide-37, pentapeptide-44, pentapeptide-45, pentapeptide-46, pentapeptide-48, pentapeptide-54, pentapeptide-56, pentapeptide-57, hexapeptide-2, hexapeptide-3, hexapeptide-9, hexapeptide-10, hexapeptide-11, hexapeptide-12, hexapeptide-17, hexapeptide-33, hexapeptide-42, hexapeptide-43, hexapeptide-47, hexapeptide-57, hexapeptide-61, hexapeptide-62, hexapeptide-63, hexapeptide-65, heptapeptide-10, heptapeptide-12, heptapeptide-13, heptapeptide-16, heptapeptide-22, heptapeptide-36, heptapeptide-37, heptapeptide-38, heptapeptide-39, heptapeptide-40, yeast polypeptide, feruloyl oligopeptide-33, tranexamoyl dipeptide-22, kojyl carboxy dipeptide-23, octapeptide-2, octapeptide-7, octapeptide-8, octapeptide-10, octapeptide-11, and octapeptide-15.

Furthermore, the ethosome encapsulates a complex of the peptide, which is a bioactive substance, and a hydrogel. When the peptide aqueous solution meets the hydrogel aqueous solution, an amine group of the peptide and a carboxyl group of the hydrogel bind to each other by an acid-base reaction to form the complex of the peptide and the hydrogel. When the complex of the peptide and the hydrogel encapsulated in the ethosome is applied to the skin, the peptide may be released slowly from the ethosome, and thus release of the peptide may be controlled.

In this regard, the hydrogel may be prepared by using a natural substance and/or a synthetic substance. For example the hydrogel may be at least one selected from the group consisting of a carbomer, agar, a collagen peptide, hyaluronic acid, starch, modified starches such as hydrolyzed starch and cross-linked starch, dextrin, gamma PGA, carrageenan, gums such as gum Arabic and xanthan gum, carboxymethyl cellulose (CMC), gelatin, pectin, alginic acid, and chitosan.

An addition ratio of the hydrogel to the peptide in the aqueous solution of the complex of the peptide and the hydrogel is preferably 0.01% to 50.0%, which means a weight ratio of the hydrogel to the peptide. In other words, the peptide and the hydrogel in the aqueous solution of the complex of the peptide and the hydrogel are preferably added at a ratio of 1:0.0001 to 1:0.5.

There are many known methods of preparing liposomes, and a film hydration method is generally used. For example, in a patent which discloses encapsulation of an extract of *Persicaria* hydropiper L. in ethosomes, the film hydration method is also used, in which lecithin and lipid are dissolved in an organic solvent and then the organic solvent is evaporated to form a film, an aqueous solution containing a drug to be encapsulated is added thereto to form liposomes. However, this method is possible at a laboratory level but not for mass-production.

Hereinafter, a method of preparing nanoethosomes is suggested. The preparation method described below is a process suitable for mass-production of nanoethosomes. The method of preparing the nanoethosomes are as follows:

a) dissolving a drug to be encapsulated in an aqueous solution;
b) dissolving a mixture of lecithin and lipid in ethanol;
c) adding the aqueous solution of a) to the lipid-dissolved solution to form a hydrated liquid crystalline phase;
d) adding purified water to the hydrated liquid crystalline phase and stirring the mixture for dispersion;
e) homogenizing the solution in a homo mixer; and
f) homogenizing the solution with a high pressure homogenizer.

In more detail, when the drug to be encapsulated is dissolved in the aqueous solution in a), a concentration of the drug may be preferably 1% to 10% of the aqueous solution, but may be determined depending on solubility of the drug. A proportion of the aqueous solution with respect to all components is preferably 1 wt % to 20 wt %. However, as the proportion of the aqueous solution is higher, efficiency of the drug to be encapsulated in phospholipids is lower, and therefore, the proportion is most preferably 2 wt % to 8 wt %. Accordingly, the proportion of the bioactive material in all ethosome components is preferably 0.0001 wt % to 10 wt %.

In b), a ratio of the phospholipids to be dissolved in ethanol is preferably 10 wt % to 30 wt %. Here, the ratio means a weight ratio of the phospholipids to ethanol. In other words, the ratio of the phospholipids to ethanol is preferably 1:0.1 to 1:0.3. Furthermore, the ratio of the phospholipids to be dissolved in ethanol is most preferably 20 wt % to 30 wt %. In other words, the ratio of the phospholipids to ethanol is most preferably 1:0.2 to 1:0.3. When the ratio of the phospholipids to be dissolved in ethanol is as low as 10% or less, the proportion of ethanol in the total components is high. When the ratio of the phospholipids to be dissolved in ethanol is too high, the proportion of ethanol in the total components is too low. Therefore, it is necessary to control the ratio. Accordingly, the proportion of ethanol in the entire ethosome solution is 20 wt % or less.

In c), a ratio of the solution of a) and the solution of b) is important. A ratio of the solution of b) (lipid-dissolved solution) to the solution of a) (drug aqueous solution) is preferably 1:0.1 to 1:10. Furthermore, the ratio of the solution of b) (lipid-dissolved solution) to the solution of a) (drug aqueous solution) is most preferably 1:0.5 to 1:2.

In d), purified water is added to the hydrated liquid crystalline phase prepared in c) under stirring. In d), while slowly stirring the hydrated liquid crystalline phase, a proportion of purified water in all components is preferably 10 wt % to 95 wt %. Furthermore, the proportion of purified water in all components is most preferably 60 wt % to 90 wt %. 60 wt % to 90 wt % of purified water is the most proper proportion in that phospholipids cause a phase transition to encapsulate the drug, resulting in formation of nanoparticles.

e) is a process of performing particle homogenization through a primary homo mixer, and is performed for about 5 minutes to about 10 minutes at 3,000 rpm to 5000 rpm. Through this process, more homogeneous particles may be formed during encapsulation of the drug in phospholipids dissolved in ethanol.

f) is a process of further homogenizing the ethosome solution at a smaller size by using a high pressure homogenizer. A pressure condition of the high pressure homogenizer is preferably 100 bar or more, and the number of passage is preferably once or more. The pressure condition of the high pressure homogenizer is most preferably 1000 bar, and the number of passage is most preferably three times or more. The process of using the high pressure homogenizer is a process that is very important in the formation of the nanoparticles and is suitable for mass-production.

Ethosomes described below are able to remarkably improve drug encapsulation efficiency and stability, as compared with known ethosomes. Further, as compared with known ethosomes, high content of the ethosomes may be included in cosmetics by optimizing the ethanol content without causing skin irritation as a cosmetic ingredient. According to the technology described below, a problem of nanoparticle size increase which may occur at a low content of ethanol may be solved by treatment of a high pressure homogenizer, leading to reduction in the particle size and further increase of transdermal absorption rate. The technology described below enables commercialization of ethosomes as a cosmetic ingredient by developing a method of preparing the ethosome, which is suitable for mass-production. The technology described below provides a cosmetic ingredient very effective for wrinkle improvement by developing nanoethosomes including palmitoyl pentapeptide and acetyl hexapeptide which are wrinkle-improving peptides.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of", when preceding a list of elements, modify the entire list of elements and do not modify the individual elements of the list.

BRIEF DESCRIPTION OF DRAWINGS

These and/or other aspects will become apparent and more readily appreciated from the following description of the embodiments, taken in conjunction with the accompanying drawings in which:

FIG. 1 illustrates example structures of a known liposome (a) and a novel nanoethosome (b);

FIG. 2 shows experimental results of analysis of particle sizes of prepared ethosomes;

FIG. 3 shows photographs showing experimental results of a stability test of the prepared ethosomes after 30 days;

FIG. 4 is a graph showing experimental results of an encapsulation efficiency test of the prepared ethosomes;

FIG. 5 is a graph showing experimental results of a collagen production test of the prepared ethosomes;

FIG. 6 is a photograph showing results of evaluation of wrinkle improvement before and at 4 weeks after application of the nanoethosome solution; and FIG. 7 is respectively show graphs showing results of evaluation of wrinkle improvement (a) and elasticity improvement (b) of subjects before and at 2 weeks and 4 weeks after application of the nanoethosome solution.

MODE FOR THE INVENTION

Hereinafter, an ethosome delivery system prepared by the above-described processes will be described with reference to Examples. The following Examples describes a peptide, a hydrogel, a lipid, a solvent, etc., which is limited to a specific substance. However, as described above, various other types of the peptide, hydrogel, lipid, solvent, etc. may be used.

EXAMPLE 1

Palmitoyl pentapeptide-4 was added to and dissolved in purified water. Since palmitoyl pentapeptide-4 was hardly dissolved in purified water, a small amount of lactic acid was added thereto to easily dissolve palmitoyl pentapeptide-4 (preparation of a peptide aqueous solution). The peptide was dissolved such that a content thereof in all ethosome components was 0.1 wt %.

To the dissolved peptide aqueous solution, 1 wt % of a carbomer aqueous solution was added, and dispersed with a magnetic stirrer of 700 rpm under environments at 70° C. A content of the carbomer in all ethosome components was 0.005 wt %. Through these processes, a peptide-hydrogel complex dispersion solution was prepared.

Ethanol was added such that its content in the ethosome solution was 4 wt %. Cholesterol and dicetyl phosphate were added to ethanol and dissolved with a magnetic stirrer of 300 rpm under environments at 50° C. Hydrogenated lecithin was added to the dissolved solution, and dissolved with a magnetic stirrer of 300 rpm under environments at 70° C. to prepare a transparent solution phase (a lipid-dissolved solution).

The peptide-hydrogel complex dispersion solution was added to the lipid-dissolved solution, and mixed well for 5 minutes or more to dehydrate the lipid solution phase, and as a result, a hydrated liquid crystalline phase was prepared.

To the hydrated liquid crystalline phase, purified water was added and stirred for 1 hour or more, and pH thereof was adjusted from 6.0 to 7.5 by using a 1 N NaOH aqueous solution to prepare a peptide-hydrogel-encapsulated nano-ethosome solution.

The prepared solution was homogenized by using a homo mixer at 5000 rpm for 5 minutes, and then further homogenized by using a high pressure homogenizer at a pressure of 1000 bar and the number of passage of three times. After completing the homogenization, the solution was slowly cooled in a water bath.

EXAMPLE 2

In Example 2, ethosomes were prepared in the same manner as in Example 1, except that the content of ethanol was changed to 2 wt %.

EXAMPLE 3

Example 3 is an example of using acetyl hexapeptide-8 and palmitoyl pentapeptide-4 at a ratio of 1:1. Acetyl hexapeptide-8 and palmitoyl pentapeptide-4 were added in an amount of 0.5 wt %, respectively and other procedures were performed in the same manner as in Example 1.

EXAMPLE 4

In Example 4, ethosomes were prepared in the same manner as in Example 3, except that carbomer which is a hydrogel was not added.

EXAMPLE 5

Cosmetic ingredient compositions were prepared by adding the cosmetic compositions prepared in Examples 1 to 4.

EXAMPLE 6

A cosmetics including the cosmetic ingredient compositions prepared in Example 5 was prepared.

In the following Table 1, the above-described components of Examples 1 to 4 and homogenization are summarized.

TABLE 1

| | (Unit: wt %) | | | |
|---|---|---|---|---|
| Component | Example 1 | Example 2 | Example 3 | Example 4 |
| Lecithin | 1 | 1 | 1 | 1 |
| Cholesterol | 0.1 | 0.1 | 0.1 | 0.1 |
| Dicetyl phosphate | 0.05 | 0.05 | 0.05 | 0.05 |
| Palmitoyl pentapeptide-4 | 0.1 | 0.1 | 0.05 | 0.05 |
| Acetyl hexapeptide-8 | — | — | 0.05 | 0.05 |
| Carbomer | 0.005 | 0.005 | 0.005 | — |
| Ethanol | 4 | 2 | 4 | 4 |
| purified water | Up to 100 | Up to 100 | Up to 100 | Up to 100 |
| Homogenization | ○ | ○ | ○ | ○ |

COMPARATIVE EXAMPLE 1

In Comparative Example 1, ethosomes were prepared in the same manner as in Example 1, except that the content of ethanol was changed to 20 wt %.

COMPARATIVE EXAMPLE 2

In Comparative Example 2, the homogenization process was omitted from the procedures of Example 3. In other words, the peptide-encapsulated ethosome solution was used as it is without homogenization by the high pressure homogenizer.

In the following Table 2, the composition ratios of Comparative Examples 1 to 2 and homogenization are summarized.

TABLE 2

(Unit: wt %)

| Component | Comparative Example 1 | Comparative Example 2 |
|---|---|---|
| Lecithin | 1 | 1 |
| Cholesterol | 0.1 | 0.1 |
| Dicetyl phosphate | 0.05 | 0.05 |
| Palmitoyl pentapeptide-4 | 0.05 | 0.05 |
| Acetyl hexapeptide-8 | 0.05 | 0.05 |
| Carbomer | 0.005 | 0.005 |
| Ethanol | 20 | 4 |
| purified water | Up to 100 | Up to 100 |
| Homogenization | X | X |

The nanoethosomes of Examples and Comparative Examples were subjected to pre-determined experiments.

Experimental results will be described in Experimental Examples below.

Experimental Example 1: Ethosome Particle Size according to Formulation Composition Ratio and High Pressure Homogenization To analyze average particle sizes of the nanoethosomes prepared in Examples and Comparative Examples, a nanoparticle analyzer (NICOMP 380ZLS, Santa Barbara) was used to measure their particle sizes, and results are shown in Table 3.

FIG. 2 shows results of analysis of particle sizes. FIG. 2(a) shows the result of Comparative Example 2, and FIG. 2(b) shows the result of Example 3. The size of Examples 1 to 4 was approximately 250 nm or less. The preferred size of ethosome particle is 50 nm to 1000 nm.

Example 1 and Example 2 suggest that as the content of ethanol is lower, the particle size is larger, and Example 3 and Example 4 suggest that the particle size is increased by addition of hydrogen. As Example 3 is compared with Comparative Example 2, the particle size was decreased by homogenization through the high pressure homogenizer. When 20 wt % of ethanol was added in Comparative Example 1, aggregation occurred and no ethosomes were formed.

TABLE 3

| | Particle size (nm) |
|---|---|
| Example 1 | 161.1 |
| Example 2 | 220.3 |
| Example 3 | 248.2 |
| Example 4 | 195.9 |
| Comparative Example 1 | Aggregation |
| Comparative Example 2 | 853.1 |

Experimental Example 2: Stability According to Formulation Composition Ratio and High Pressure Homogenization First, stabilities of the prepared ethosome solutions were tested. Stabilities of the prepared nanoethosomes were measured to examine discoloration, phase separation, etc. under particular conditions over time. FIG. 3 shows results of a stability test of the prepared ethosomes over time. FIG. 3(a) is a photograph showing the peptide-hydrogel complex ethosome of Example 3 after 30 days. FIG. 3(b) is a photograph showing the peptide ethosome of Example 4 after 30 days.

Experimental conditions are as follows. The ethosome solutions prepared in Examples and Comparative Examples were placed in a constant temperature chamber maintained at 45° C. Changes of these ethosome solutions were observed at time points of 1 day, 10 days, 20 days, and 30 days. Discoloration, phase separation, etc. of the ethosome solutions were examined over time. Experimental results are as in the following Table 4.

TABLE 4

| | 1 day | 10 days | 20 days | 30 days |
|---|---|---|---|---|
| Example 1 | Stable | Stable | Stable | Stable |
| Example 2 | Stable | Stable | Stable | Stable |
| Example 3 | Stable | Stable | Stable | Stable |
| Example 4 | Stable | Stable | Stable | Precipitation |
| Comparative Example 1 | Precipitation | Precipitation | Precipitation | Precipitation |
| Comparative Example 2 | Opaque | Precipitation | Precipitation | Precipitation |

Referring to the results of Table 4, Example 1 to Example 3 showed a stable shape in a transparent solution phase at day 1, and no discoloration and no phase separation for 30 days. Furthermore, Example 4 showed a transparent solution phase at day 1, but precipitation was observed and stability was reduced at about 20 days. Comparative Example 2 showed an opaque solution phase at day 1, but precipitation was observed at about 10 days.

Experimental Example 3: Measurement of Encapsulation Efficiency of Formulated Nanoethosome The ethosome solutions prepared in Examples and Comparative Examples were centrifuged at 4° C. and 17,000 rpm for 1 hour to separate supernatants and precipitates. Thereafter, the supernatants were collected and concentrations of peptides not encapsulated were measured. Encapsulation efficiency was calculated by the following Equation:

$$\text{Encapsulation efficiency } (\%) = (E_1 - E_A)/E_1 * 100$$

$E_A$: Concentration of peptide of supernatant after centrifugation $E_1$: Concentration of initially added peptide FIG. 4 is a graph showing experimental results of an encapsulation efficiency test of the prepared ethosomes. Table 5 shows numerical values of encapsulation efficiencies measured as the experimental results.

TABLE 5

| | Encapsulation efficiency (%) |
|---|---|
| Example 1 | 67.1 |
| Example 2 | 77.2 |
| Example 3 | 92.7 |
| Example 4 | 92.4 |
| Comparative Example 1 | Not measurable |
| Comparative Example 2 | 54.2 |

Referring to Table 5, Example 1 to Example 2 showed encapsulation efficiency of 60% or more, and Example 3 to Example 4 showed encapsulation efficiency of 90% or more, indicating that higher encapsulation efficiency was observed when encapsulation was performed by using both palmitoyl pentapeptide-4 acetyl and hexapeptide-8, as compared with use of palmitoyl pentapeptide-4 alone. This is because the total content of peptides was the same at 0.1 wt % but the content of palmitoyl pentapeptide-4 was decreased. The ethosome of Comparative Example 2 which was not passed through the high pressure homogenizer showed low encapsulation efficiency, which was caused by some unstable ethosomes which were not homogenized.

Experimental Example 4: Cell Experiment for Collagen Producing Effect of Nanoethosome The nanoethosome of Example 3 which was prepared by adding acetyl hexapeptide-8 and palmitoyl pentapeptide-4 at a ratio of 5:5 was used to perform an in vitro collagen production test. Normal human dermal fibroblasts (nHDFs) were used, and to determine a concentration of a test solution, normal human dermal fibroblasts were treated with the sample material for 24 hours, and a range of the concentration at which cytotoxicity was not observed was confirmed by a cytotoxicity test. Normal human dermal fibroblasts were treated with the test solution at the determined concentration in the same manner, and mRNA expression levels of COL1A1 which is a collagen gene and MMP1 were analyzed by Real Time-PCR (RT-PCR). FIG. 5 shows results of the collagen production test.

As a result, COL1A1 mRNA expression was increased to 38.44±3.81% at a concentration of 0.05%, as compared with a negative control, indicating increased collagen production, and MMP1 mRNA expression was decreased to 21.05±0.62% at a concentration of 0.05%, as compared with the negative control, indicating decreased collagenase production.

Experimental Example 5: Human Body Application Test of Nanoethosome for Wrinkle and Elasticity Improvement The nanoethosome of Example 3 which was prepared by adding acetyl hexapeptide-8 and palmitoyl pentapeptide-4 at a ratio of 5:5 was applied to humanbodies to test wrinkle and elasticity improvement.

The nanoethosome solution was evenly applied and absorbed to 23 women aged 39 to 61 years after morning and evening cleansing for 4 weeks, and improvement of wrinkles and elasticity was evaluated at 2 and 4 weeks. FIG. 6 is a photograph showing the result of testing wrinkle improvement before and at 4 weeks after application of the nanoethosome solution. FIG. 7 is a graph showing the result of testing wrinkle and elasticity improvement of the subjects before and at 2 weeks and 4 weeks after application of the nanoethosome solution. FIG. 7(a) is a graph showing the result of testing wrinkle improvement of the subjects and FIG. 7(b) is a graph showing the result of testing elasticity improvement of the subjects.

To measure wrinkles medium values indicating skin's wrinkles, ANTERA 3D (Miravex, Ireland) was used for evaluation, and wrinkles were reduced to 9.99% at 2 weeks after application and 10.82% at 4 weeks after application, as compared with wrinkles before application.

To measure CoR values indicating skin's elasticity, Ballistometer (Ballistometer BLS780, Dia-Stroh Ltd., UK) was used for evaluation, and elasticity was increased to 1.79% at 2 weeks after application and 3.36% at 4 weeks after application, as compared with elasticity before application.

Referring to the results of Examples and Experimental Examples, nanoethosomes with low irritation were formulated by optimizing the addition amounts of phospholipid and lipid and reducing the content of ethanol by the above-described preparation method. High encapsulation efficiency and stability, and nanosize were confirmed and collagen production effect was also confirmed, and as a result, it can be seen that the nanoethosomes may be applied as a functional cosmetic delivery system.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

The invention claimed is:

1. A method of preparing a bioactive substance-encapsulated ethosome, the method comprising:
    preparing an aqueous solution of a bioactive substance comprising a peptides-hydrogel complex formed by binding an amine group of the peptides and a carboxyl group of the hydrogel, wherein the hydrogel is a carbomer;
    preparing a lipid-dissolved solution by dissolving lipids in ethanol, wherein the lipids comprise phospholipids;
    preparing a hydrated liquid crystalline phase by hydrating the lipid-dissolved solution by mixing and agitating the aqueous solution of the bioactive substance together with the lipid-dissolved solution; and
    preparing a bioactive substance-encapsulated ethosome solution by adding purified water to the hydrated liquid crystalline phase to produce a mixture and agitating the mixture, wherein in the step of preparing the ethosome solution, the peptides-hydrogel complex is encapsulated inside the ethosome to generate the bioactive substance-encapsulated ethosome,
    wherein a content of the phospholipids in the ethosome solution is 0.1 wt % to 10 wt %, and wherein a content of the ethanol in the ethosome solution is 2 wt % to 8 wt %, and wherein a content of the hydrogel in the ethosome solution is 0,005 wt %.

2. The method of preparing the bioactive substance-encapsulated ethosome of claim 1, wherein a content of the bioactive substance in the ethosome solution is 0.0001 wt % to 10 wt %.

3. The method of preparing the bioactive substance-encapsulated ethosome of claim 1, wherein a weight ratio of the peptides and the hydrogel in the peptides-hydrogel complex is 1:0.0001 to 1:0.5.

4. The method of preparing the bioactive substance-encapsulated ethosome of claim 1, wherein a weight ratio of the ethanol and the lipids in the lipid-dissolved solution is 1:0.1 to 1:0.3.

5. The method of preparing the bioactive substance-encapsulated ethosome of claim 1, wherein, in the hydrated liquid crystalline phase, a ratio of the aqueous solution of the bioactive substance to the lipid-dissolved solution is 1:0.1 to 1:10 by weight.

6. The method of preparing the bioactive substance-encapsulated ethosome of claim 1, further comprising adding an alkaline aqueous solution to the hydrated liquid crystalline phase to adjust pH of the ethosome from 6.0 to 7.5.

7. The method of preparing the bioactive substance-encapsulated ethosome of claim 1, further comprising homogenizing the ethosome solution.

8. The method of preparing the bioactive substance-encapsulated ethosome of claim 7, wherein the homogenization comprises primarily homogenizing the ethosome solution by using a homo mixer at 3,000 rpm to 5,000 rpm for 5 minutes to 10 minutes and further homogenizing the primarily homogenized solution by using a high-pressure homogenizer.

9. The method of preparing the bioactive substance-encapsulated ethosome of claim 1, wherein the peptides are acetyl hexapeptide and palmitoyl pentapeptide.

10. The method of preparing the bioactive substance-encapsulated ethosome of claim 9, wherein a ratio of the acetyl hexapeptide to the palmitoyl pentapeptide is 1:1 by weight.

* * * * *